United States Patent [19]

Yeakey et al.

[11] Patent Number: 4,482,743

[45] Date of Patent: Nov. 13, 1984

[54] HYDROXYALKYL BIS(DIALKYLAMINOALKYL)AMINE MANUFACTURE

[75] Inventors: Ernest L. Yeakey; Robert L. Zimmerman, both of Austin, Tex.

[73] Assignee: Texaco Inc., White Plains, N.Y.

[21] Appl. No.: 518,170

[22] Filed: Jul. 28, 1983

[51] Int. Cl.$^3$ .................... C07C 85/00; C07C 85/02; C07C 85/18
[52] U.S. Cl. .................................................. 564/477
[58] Field of Search ......................................... 564/477

[56] References Cited

U.S. PATENT DOCUMENTS

| | | | |
|---|---|---|---|
| 2,046,720 | 7/1936 | Bottoms | 564/477 X |
| 3,200,154 | 8/1965 | Kirkpatrick et al. | 564/477 X |
| 3,364,262 | 1/1968 | Cyba | 564/477 X |
| 3,723,530 | 3/1973 | Goetze et al. | 564/477 |
| 3,761,523 | 9/1973 | Reid et al. | 564/477 |

*Primary Examiner*—Paul F. Shaver
*Attorney, Agent, or Firm*—Jack H. Park; Kenneth R. Priem; David L. Mossman

[57] ABSTRACT

A process for manufacturing hydroxyalkyl bis(dialkylaminoalkyl)amine is disclosed wherein dialkylaminopropylaminopropionitrile is separated from a mixture of dialkylaminopropylaminopropionitrile and bis(dialkylaminoalkyl)amine by adding to the mixture under alkoxylation conditions alkylene oxide sufficient to react with substantially all of the bis(alkylaminoalkyl)amine and then separating the reacted materials by distillation. This process yields very pure hydroxyalkyl bis(dialkylaminoalkyl)amine which is useful as a urethane catalyst.

6 Claims, No Drawings

HYDROXYALKYL BIS(DIALKYLAMINOALKYL)AMINE MANUFACTURE

BACKGROUND OF THE INVENTION

1. Field of the Invention

This invention pertains to the field of catalyst manufacture.

2. Description of the Prior Art

Hydroxyalkyl bis(dialkylaminoalkyl)amine is disclosed as a useful urethane catalyst in U.S. Pat. No. 4,101,470. The patent discloses that these compositions may be prepared by first making bis(dialkylaminopropyl)amine which may be readily reacted with various olefin oxides. However, it has been found that in the manufacture of the bis(dialkylaminopropyl)amines by the reaction of a dialkylamine with acrylonitrile followed by hydrogenation that a significant quantity of dimethylaminoalkylaminoalkylnitrile is also produced. This is difficult to separate from the bis(dialkylaminopropyl)amine.

The invention disclosed herein provides a method whereby very pure hydroxyalkyl bis(dialkylaminoalkyl)amine is made.

SUMMARY OF THE INVENTION

The invention is a process for preparing relatively pure hydroxyalkyl bis(dialkylaminoalkyl)amine by adding to a mixture of dialkylaminoalkylaminoalkylnitrile and bis(dialkylaminoalkyl)amine under alkoxylation conditions sufficient alkylene oxide to react with substantially all of the bis(dialkylaminoalkyl)amine and then separating the reacted materials by distillation.

DESCRIPTION OF THE PREFERRED EMBODIMENTS

In one embodiment of the invention, bis(dialkylaminopropyl)amine, represented by the structure

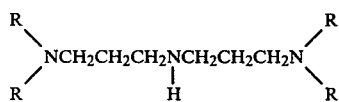

and dialkylaminopropylaminopropionitrile, represented by the structure

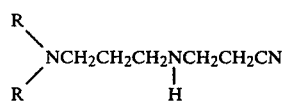

where R is lower alkyl in both structures, are reacted with an alkylene oxide which preferentially reacts with the bis(dialkylaminopropyl)amine. The products are then separated by distillation.

A preferred embodiment is the following reaction sequence which produces a mixture of dimethylaminopropylamine (A), bis(dimethylaminopropyl)amine (B) and dimethylaminopropylaminopropionitrile (C)

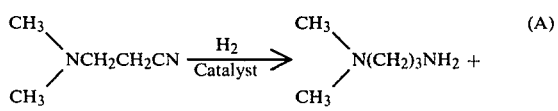

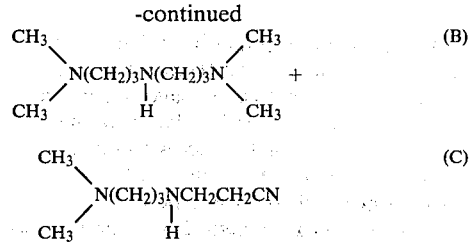

(A) can be separated readily from B and C by distillation; however, it is very difficult to separate B from C by distillation.

In this invention an alkylene oxide such as ethylene oxide, propylene oxide, butylene oxide or the like (preferably propylene oxide) is reacted with the mixture of bis(dialkylaminoalkyl)amine and the dimethylaminoalkylaminoalkylnitrile under conventional alkoxylation conditions and the alkylene oxide reacts with substantially all of the bis(dialkylaminoalkyl)amine in preference to the nitrile compound. The resulting hydroxyalkyl bis(dialkylaminoalkyl)amine has the following structure if propylene oxide, for example, is used

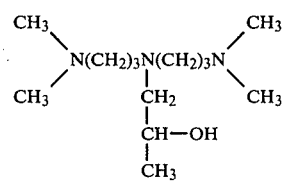

This compound may then be separated from the nitrile compound by simple distillation techniques resulting in a relatively pure hydroxyalkyl derivative of the bis(dialkylaminoalkyl)amine.

The following examples this separation technique.

EXAMPLE 1

The amines were charged to a kettle and then heated to 130° C. The propylene oxide was then added while maintaining the reaction temperature between 130° C. and 140° C. After all of the propylene oxide had been added, the reaction was digested to a constant pressure and then cooled and discharged.

| | A | B | C | D | E |
|---|---|---|---|---|---|
| Reactants | | | | | |
| bis(dimethylaminopropyl)amine | 200 | 200 | 200 | 200 | 200 |
| Dimethylaminopropylaminopropionitrile | 20 | 20 | 20 | 20 | 20 |
| Water | — | 4.0 | 4.0 | 4.0 | — |
| Propylene oxide | 37.2 | 37.2 | 62 | 49.6 | 62.1 |
| Gas Chromatogram, area % | | | | | |
| bis(dimethylaminopropyl)amine | 43 | 56 | 33 | 44 | 21 |
| Dimethylaminopropylaminopropionitrile | 9 | 9 | 8 | 9 | 7 |
| Hydroxypropyl bis(dimethylaminopropyl)amine | 46 | 33 | 56 | 45 | 63 |

Example B was distilled using a 9" Vigreaux column. The first distillation cut was 90°–110° C. at 2.1 mm Hg vacuum. It contained 86% bis(dimethylaminopropyl)amine and 11% dimethylaminopropylaminopropionitrile. The product hydroxypropyl bis(dimethylaminopropyl)amine was obtained at 131° C. and 2.5 mm Hg vacuum. It was 99% pure by gas chromatograph.

We claim:

1. A process for preparing relatively pure hydroxyalkyl bis(dialkylaminoalkyl)amine by adding to a mixture of dialkylaminoalkylaminoalkylnitrile and bis(dialkylaminoalkyl)amine under alkoxylation conditions sufficient alkylene oxide to react with substantially all of the bis(dialkylaminoalkyl)amine and then separating the reacted materials by distillation.

2. A process as in claim 1 wherein the alkylene oxide is propylene oxide.

3. A process for preparing hydroxyalkyl bis(dialkylaminopropyl)amine by adding to a mixture of dialkylaminopropylaminopropionitrile and bis(dialkylaminopropyl)amine under alkoxylation conditions sufficient alkylene oxide to react with substantially all of the bis(dialkylaminopropyl)amine and then separating the reacted materials by distillation.

4. A process as in claim 3 wherein the alkylene oxide is propylene oxide.

5. A process for preparing hydroxypropyl bis(dimethylaminopropyl)amine by adding to a mixture of dimethylaminopropylaminopropionitrile and bis(dimethylaminopropyl)amine under alkoxylation conditions sufficient alkylene oxide to react with substantially all of the bis(dimethylaminopropyl)amine and then separating the reacted materials by distillation.

6. A process as in claim 5 wherein the alkylene oxide is propylene oxide.

* * * * *